(12) United States Patent
O'Connor et al.

(10) Patent No.: US 6,827,095 B2
(45) Date of Patent: Dec. 7, 2004

(54) MODULAR MICROFLUIDIC SYSTEMS

(75) Inventors: Stephen D. O'Connor, Pasadena, CA (US); Christoph D. Karp, Pasadena, CA (US); Eugene Dantsker, Sierra Madre, CA (US); Marci Pezzuto, Altadena, CA (US)

(73) Assignee: Nanostream, Inc., Pasadena, CA (US)

( * ) Notice: Subject to any disclaimer, the term of this patent is extended or adjusted under 35 U.S.C. 154(b) by 0 days.

(21) Appl. No.: 10/134,119

(22) Filed: Apr. 25, 2002

(65) Prior Publication Data

US 2002/0124896 A1 Sep. 12, 2002

Related U.S. Application Data

(63) Continuation-in-part of application No. 09/689,568, filed on Oct. 12, 2000, now Pat. No. 6,536,477.
(60) Provisional application No. 60/296,882, filed on Jun. 7, 2001.

(51) Int. Cl.$^7$ .................................................. F15C 1/12
(52) U.S. Cl. ................ 137/15.01; 137/819; 137/827; 137/828; 137/833; 137/269; 137/271
(58) Field of Search ................ 137/833, 814, 137/815, 819, 269, 271, 15.01

(56) References Cited

U.S. PATENT DOCUMENTS

| | | | | |
|---|---|---|---|---|
| 3,570,511 A | * | 3/1971 | Bermel | 137/819 |
| 3,698,432 A | * | 10/1972 | Kutz | 137/884 |
| 3,942,558 A | * | 3/1976 | Honda et al. | 137/814 |
| 5,488,925 A | * | 2/1996 | Kumada | 137/884 |
| 5,640,995 A | | 6/1997 | Packard et al. | 137/597 |
| 5,727,618 A | | 3/1998 | Mundinger et al. | 165/80.4 |
| 5,748,827 A | | 5/1998 | Holl et al. | 358/134 |
| 5,755,942 A | | 5/1998 | Zanzucchi et al. | 204/454 |
| 5,839,467 A | * | 11/1998 | Saaski et al. | 137/501 |
| 5,858,194 A | | 1/1999 | Bell | 204/601 |
| 5,872,010 A | | 2/1999 | Karger et al. | 436/173 |
| 6,074,725 A | | 6/2000 | Kennedy | 428/188 |
| 6,086,740 A | | 7/2000 | Kennedy | 204/601 |
| 6,188,813 B1 | | 2/2001 | Dourdeville et al. | 385/12 |
| 6,234,191 B1 | * | 5/2001 | Clarke | 137/347 |
| 6,235,471 B1 | | 5/2001 | Knapp et al. | 435/6 |

(List continued on next page.)

FOREIGN PATENT DOCUMENTS

| | | | |
|---|---|---|---|
| EP | 1 106 244 A2 | 6/2001 | |
| WO | WO 99/19717 | 4/1999 | G01N/25/22 |

(List continued on next page.)

OTHER PUBLICATIONS

Grodzinski, P., "Development of Plastic Microfluidic Devices for Sample Preparation," presentation from BioMEMS 2000, Columbus, OH, Sep. 24, 2000.

(List continued on next page.)

*Primary Examiner*—A. Michael Chambers
(74) *Attorney, Agent, or Firm*—Vincent K. Gustafson; Michael F. Labbee

(57) ABSTRACT

A modular microfluidic system includes a plurality of discrete microfluidic modules each capable of performing at least one operation and at least one microfluidic coupling device for fluidically coupling the modules to perform a sequence of operations. The microfluidic modules and coupling devices may be constructed according to various techniques. In one embodiment, coupling devices are fabricated from multiple layers and each include a fluidic inlet port, a fluidic outlet port, and at least one sandwiched stencil layer having a microfluidic channel formed therein. Also described are integrated microfluidic systems and methods capable of performing various sequences of operations.

32 Claims, 9 Drawing Sheets

U.S. PATENT DOCUMENTS

| | | | |
|---|---|---|---|
| 6,240,790 B1 | 6/2001 | Swedberg et al. | 73/863.21 |
| 6,321,791 B1 * | 11/2001 | Chow | 137/833 |
| 6,494,614 B1 | 12/2002 | Bennett et al. | 366/336 |
| 6,533,840 B2 | 3/2003 | Martin et al. | 95/45 |
| 6,537,506 B1 | 3/2003 | Schwalbe et al. | 422/130 |
| 6,547,941 B2 | 4/2003 | Kopf-Sill et al. | 204/452 |
| 2001/0008613 A1 | 7/2001 | Kaltenbach et al. | 422/101 |
| 2004/0081583 A1 | 4/2004 | Berndt et al. | 422/63 |

FOREIGN PATENT DOCUMENTS

| | | | |
|---|---|---|---|
| WO | WO 99/60397 | 11/1999 | G01N/33/483 |
| WO | WO 00/21659 | 4/2000 | |
| WO | WO 00/51720 A3 | 9/2000 | |
| WO | WO 00/78454 | 12/2000 | B01L/3/00 |
| WO | WO 01/14064 | 3/2001 | B01L/3/00 |
| WO | WO 02/28509 | 4/2002 | B01D/53/00 |

OTHER PUBLICATIONS

Gonzalez, C., et al. "Fluidic interconnects for modular assembly of chemical microsystems," Sensors and Actuators, B 49 (1998) 40–45.

Spiering, Vincent L., et al., *Technologies and Microstructures for Separation Techniques in Chemical Analysis*, "SPIE," vol. 2882, 1996, pp. 91–100.

Hoffmann, W., et al., *Integrated microanalytical system with electrochemical detection*, "Sensors and Actuators B," 34, (1996), pp. 471–475.

Verpoorte, Elisabeth M.J., et al., "Silicon–Based Chemical Microsensors and Microsystems", *Interfacial Design and Chemical Sensing*, 1994, American Chemical Society, Chapter 21, pp. 244–254.

Cefai, J.J., et al., *Integrated chemical analysis microsystems in space life sciences research*, "J. Micromech. Microeng.," 4, (1994), pp. 172–185.

Lin, Yuehe, et al., "Microfluidic Devices on Polymer Substrates for Bioanalytical Applications," Web document published at: www.pnl.gov/microcats/aboutus/publications/microchemical/Microtechpresentation.pdf, 1999.

Gray, B., "Novel interconnection technologies for integrated microfluidic systems," Sensors and Actuators 77 (1999) 57–65.

Schuenemann, M. et al., "A highly flexible design and production framework foor modularized micromechanical systems," Sensors and Actuators 73 (1999) 153–168.

Ehrfeld, W. et al., "Potentials and Realizations of Microreactors," Aechema Monographs vol. 132 (1996).

van der Schoot, B. et al., "A modular miniaturized chemical analysis system," Sensors and Actuators B, 13–14, (1993) 333–335.

Yao, T. et al., "Micromachined Rubber O–ring Micro–fluidic Couplers," 13th IEEE International Conference on Micro Electro Mechanical Systems (MEMS '00), Miyazaki, Japan, Jan. 23–27 (2000); http://touch.caltech.edu/publications/yao/mems00/mems00.pdf.

Gonzalez, C. et al., "Fluidic interconnects for modular assembly of chemical microsystems," Sensors and Actuators B 49 (1998) 40–45.

Figeys, Daniel, *Lab–on–aChip: A Revolution in Biological and Medical Sciences*, "Analytical Chemistry," May 1, 2000.

Jeon, Noo Li et al., *Large–Area Patterning by Vacuum–Assisted Micromolding*, "Advanced Materials," 1999, No. 11.

Khandurina, Julia et al., *Microfabricated Porous Membrane Structure for Sample Concentration and Electrophoretic Analysis*, "Analytical Chemistry," vol. 71, No. 9, May 1, 1999.

Läritz, Christian et al., "A microfluidic pH–regulation system based on printed circuit board technology," *Sensors and Actuators*, 84, (2000), 230–235.

Folch, A. et al., *Molding of Deep Polydimethylsiloxane Microstructures for Microfluidics and Biological Applications*, "Transactions of the ASME," vol. 121, Feb. 1999.

"Multi–Parallel–HPLC," Web document published at: http://www.sepiatec.com/download/phplc.pdf, SEPIAtec GmbH.

MacNair, Johne E. et al., *Ultrahigh–Pressure Reversed–Phase Capillary Liquid Chromatography: Isocratic and Gradient Elution Using Columns Packed with 1.0–$\mu m$ Particles*, "Analytical Chemistry," vol. 71, No. 3, Feb. 1, 1999.

* cited by examiner

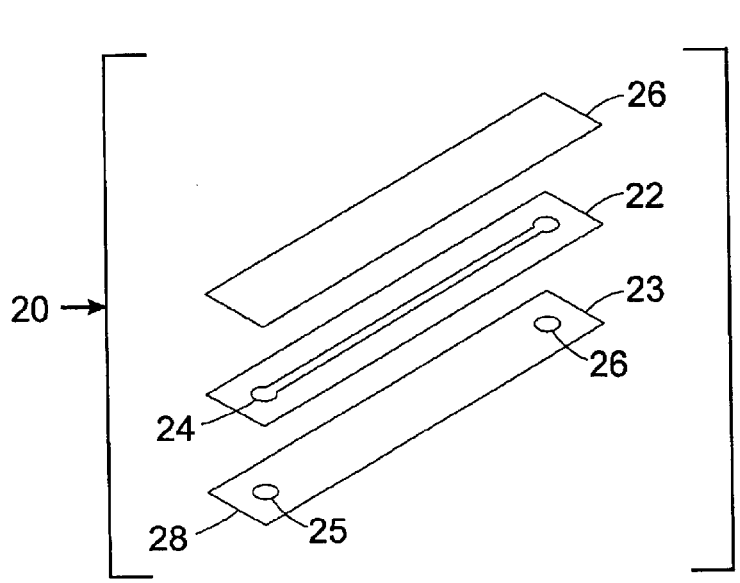
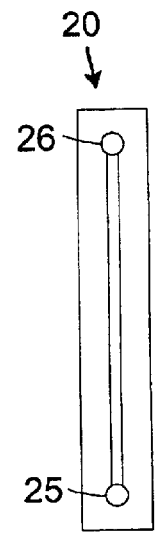
FIG._1A  FIG._1B
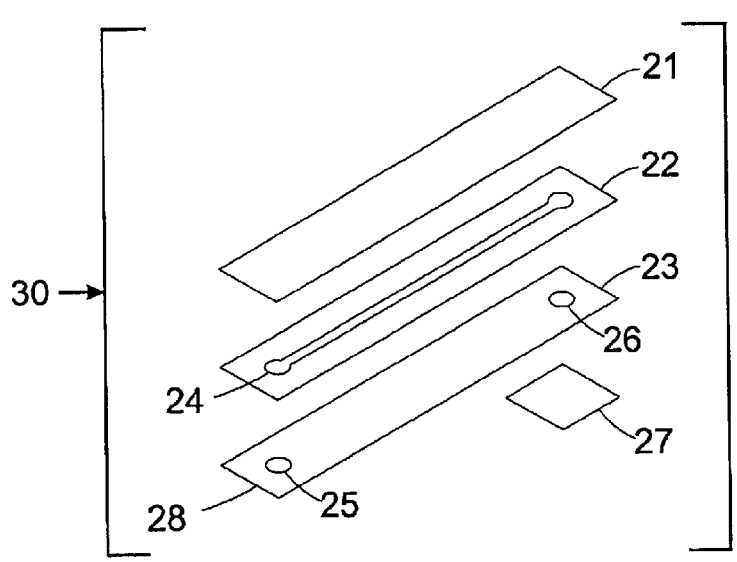
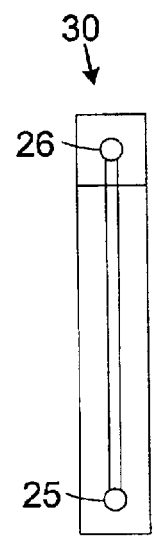
FIG._1C  FIG._1D

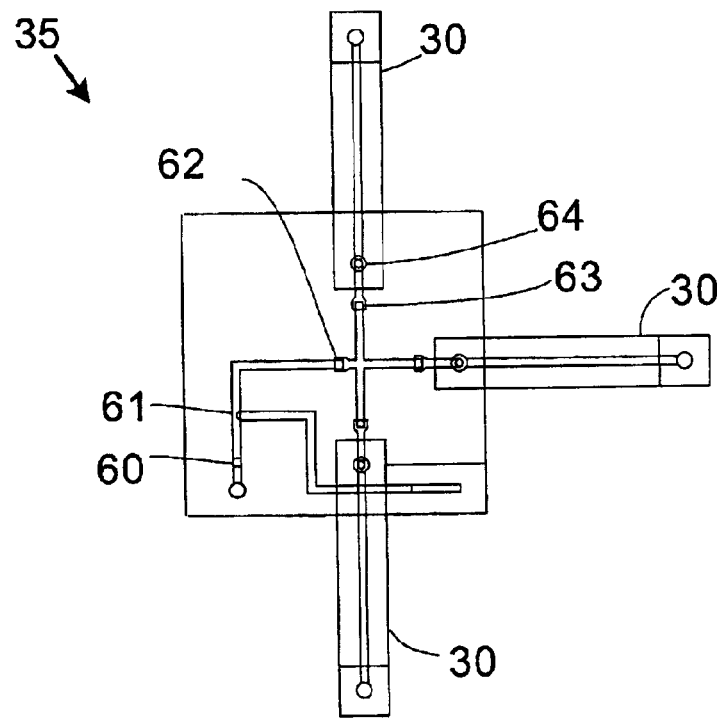
FIG._2B
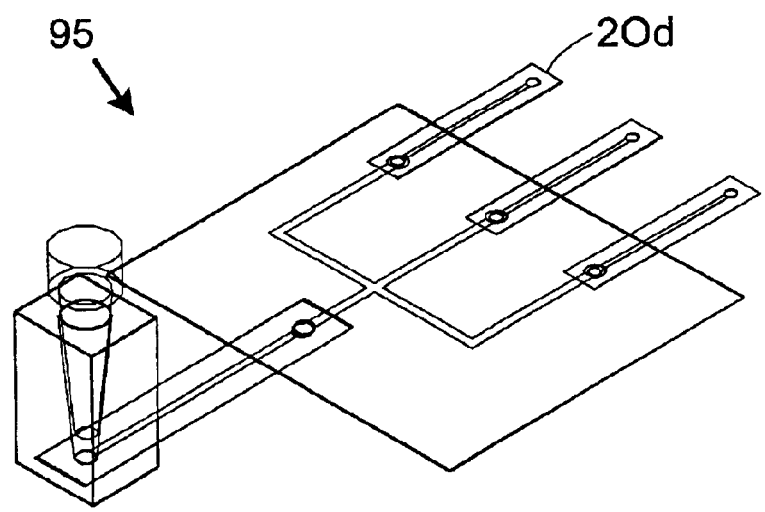
FIG._4B

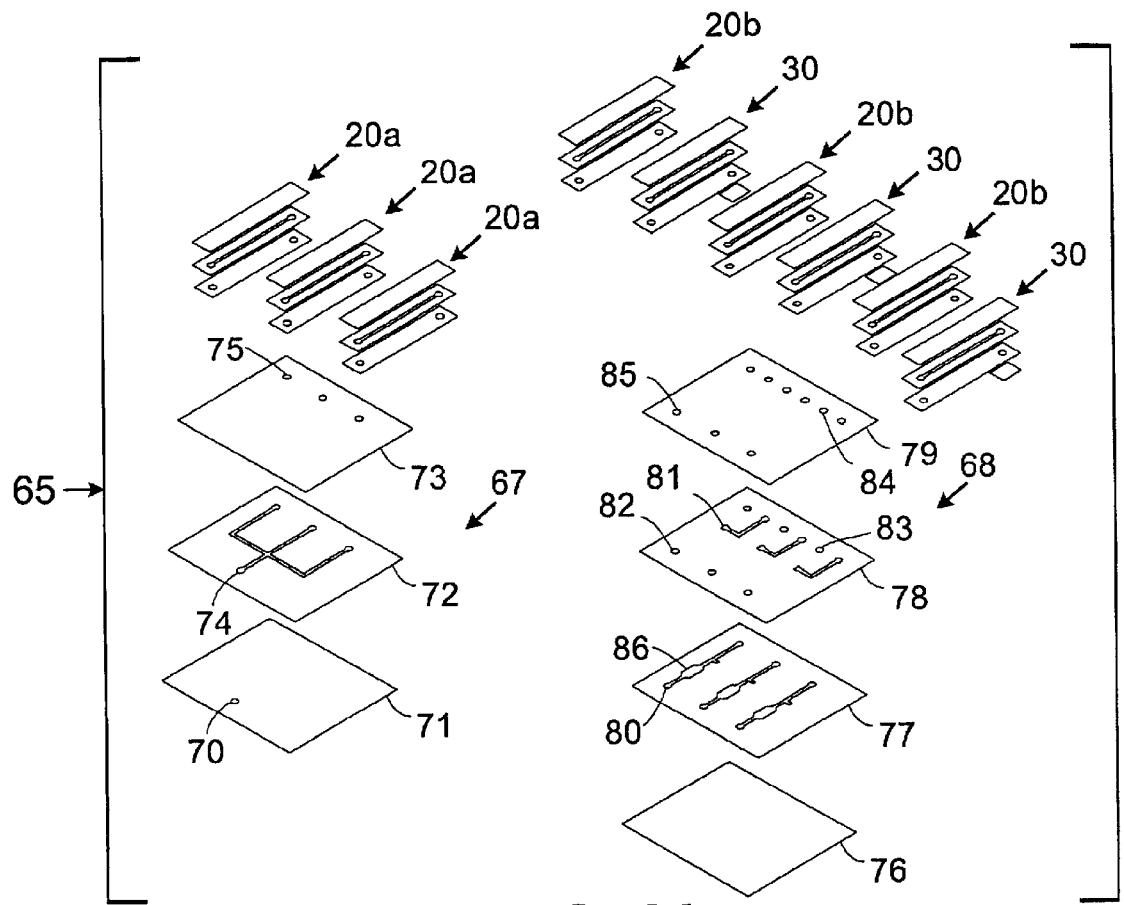
FIG._3A
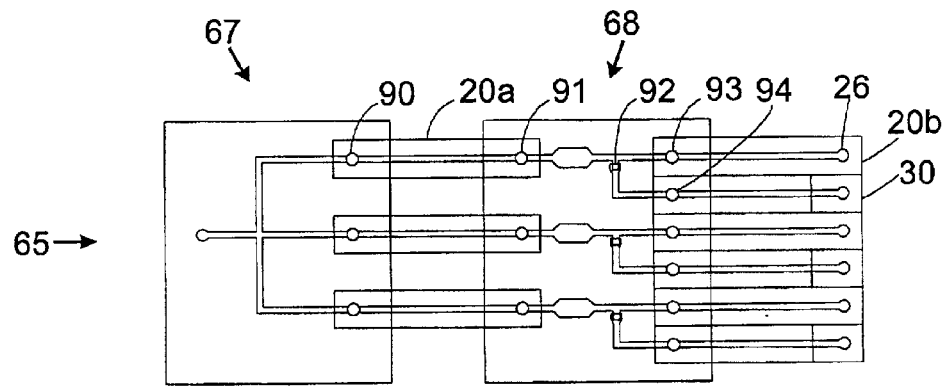
FIG._3B

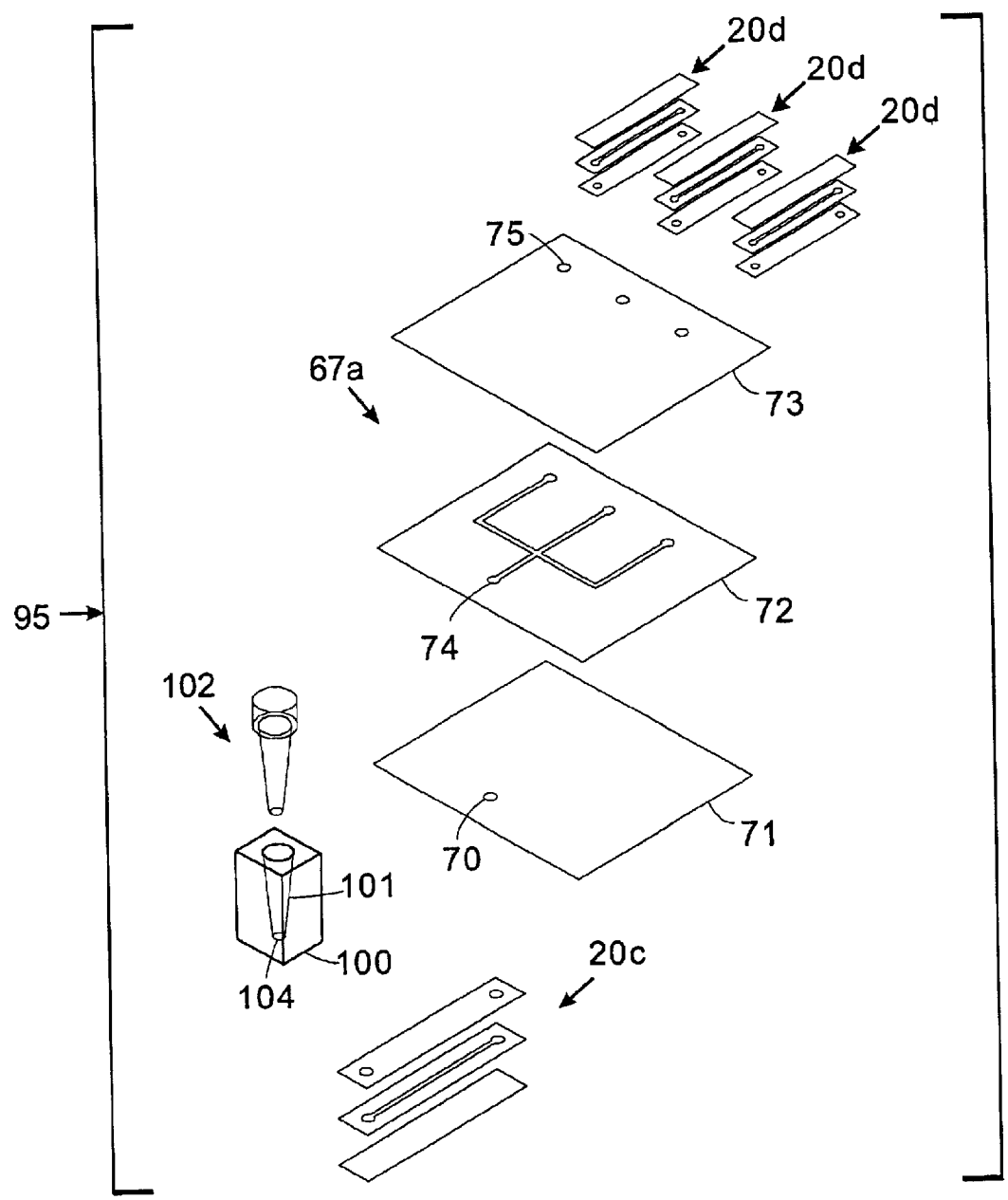
FIG._4A

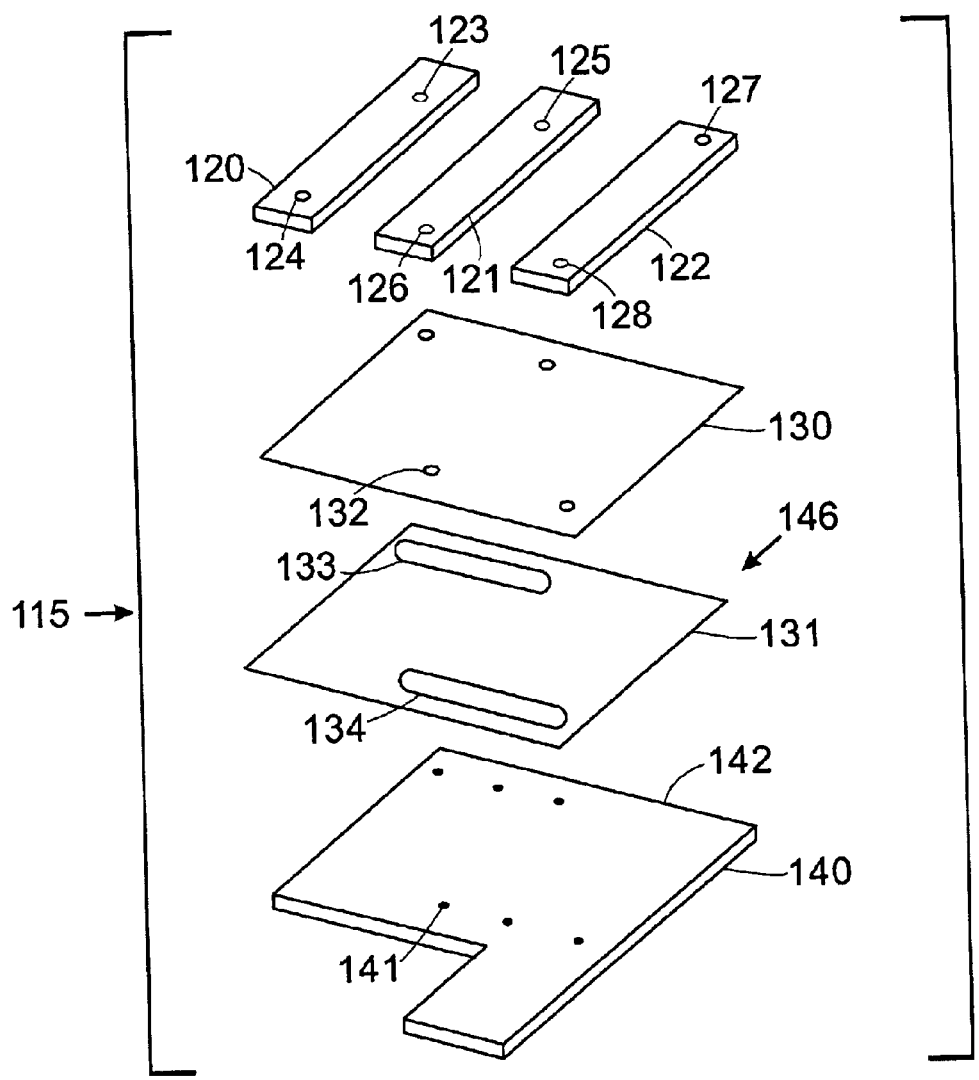
FIG._5A
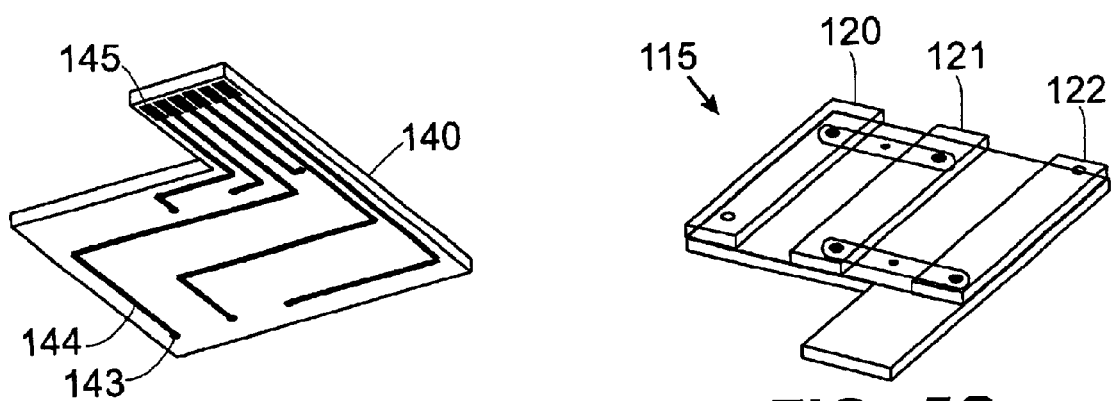
FIG._5B  FIG._5C

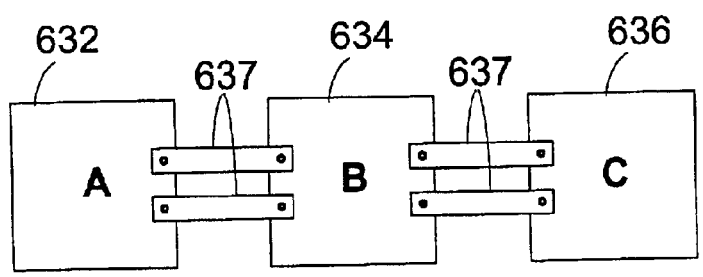
FIG._6A
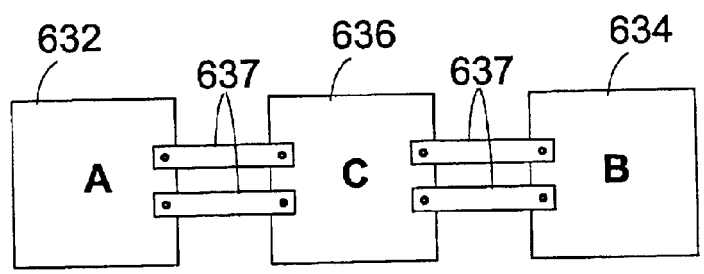
FIG._6B
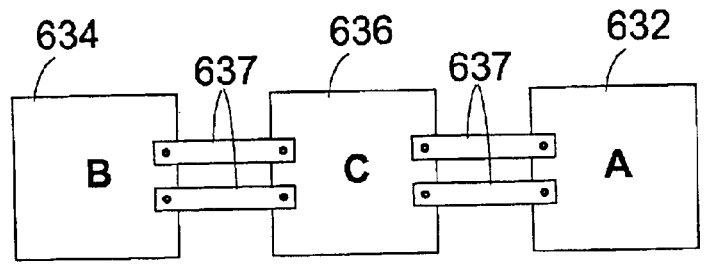
FIG._6C
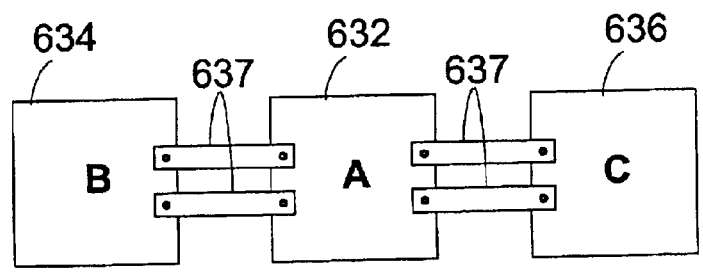
FIG._6D
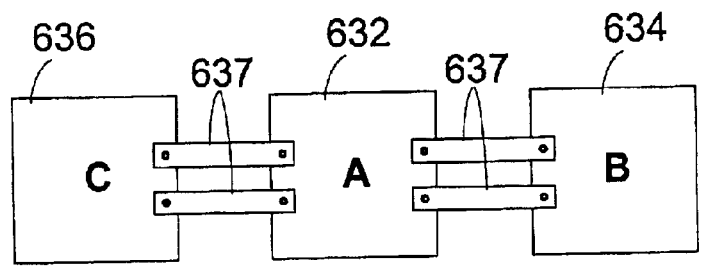
FIG._6E
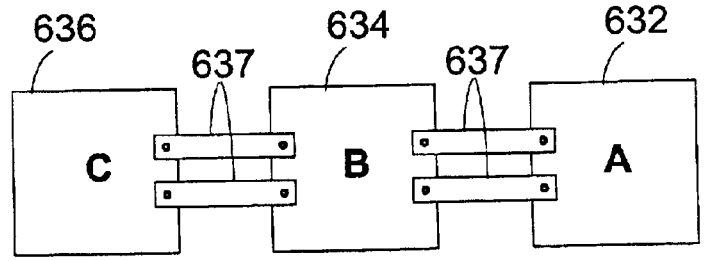
FIG._6F

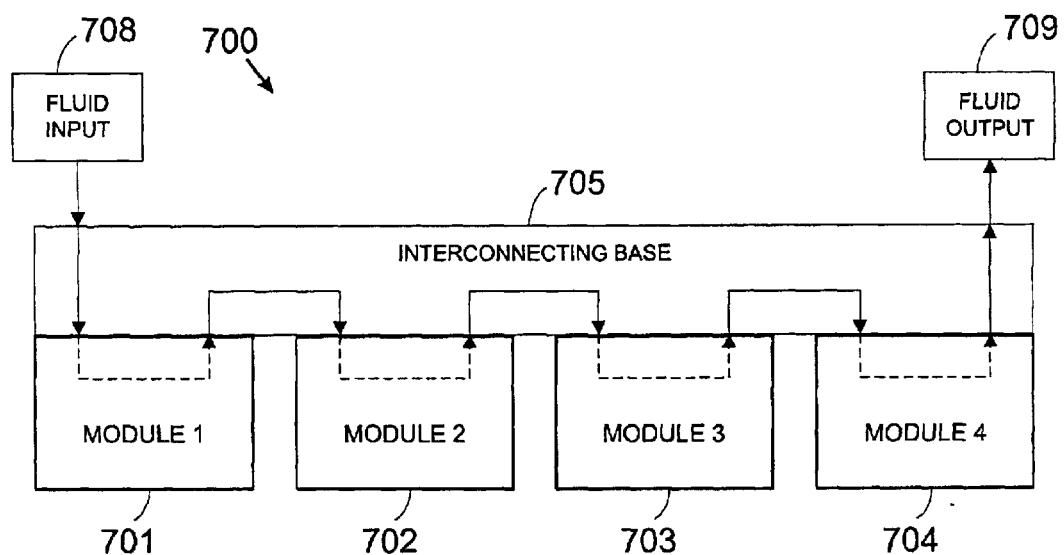
FIG._7A
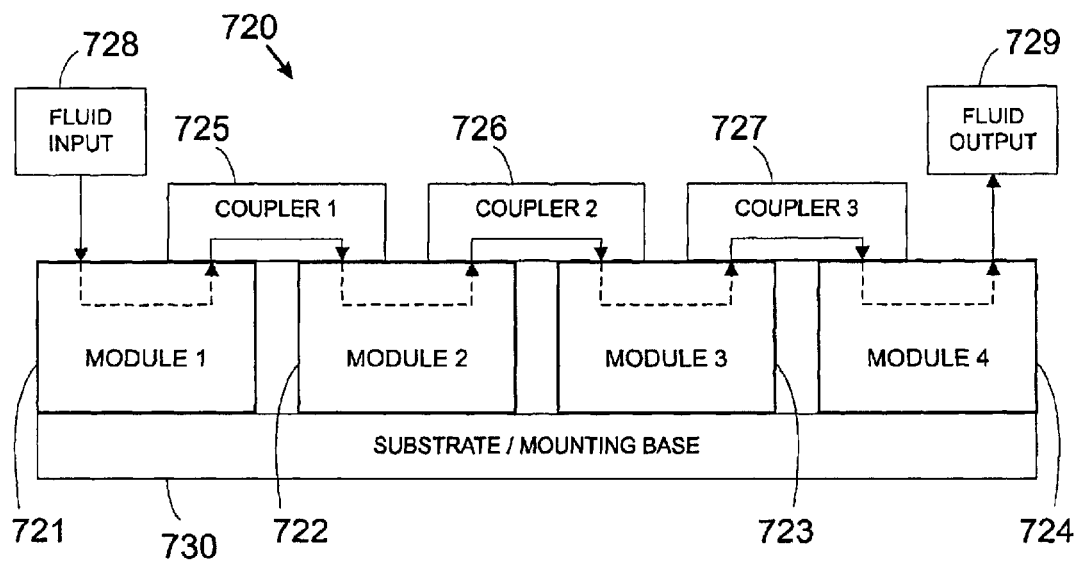
FIG._7B

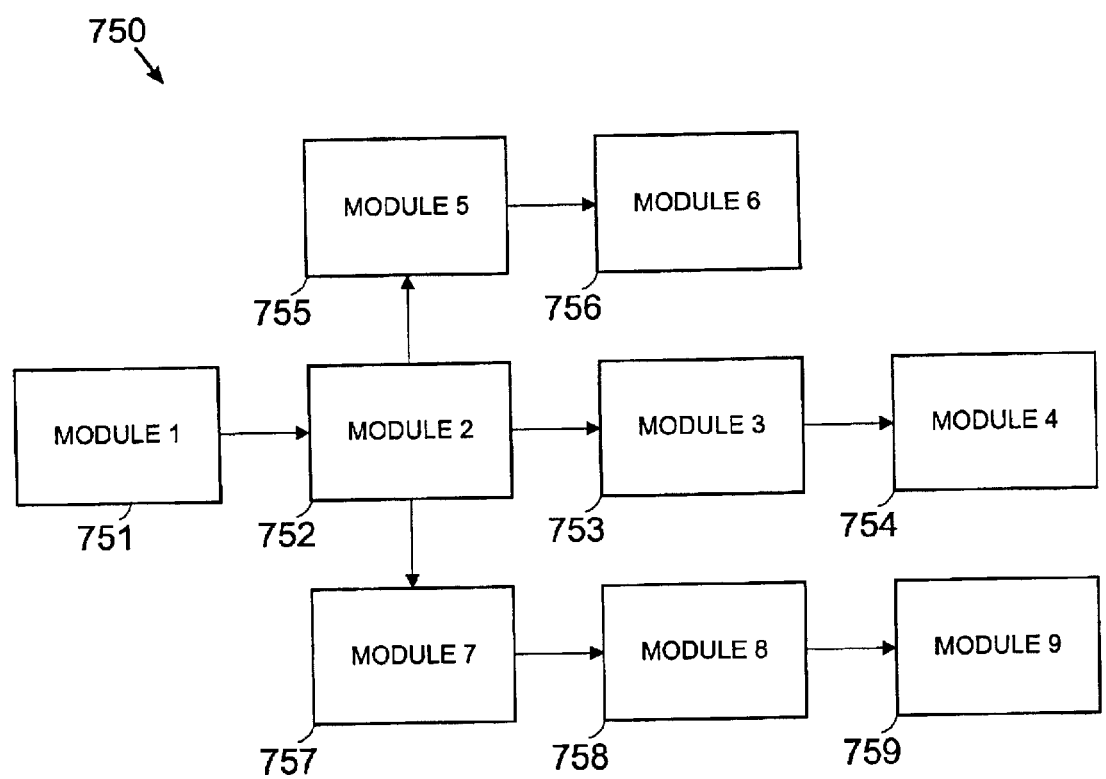
FIG._8

MODULAR MICROFLUIDIC SYSTEMS

STATEMENT OF RELATED APPLICATION(S)

This application is a continuation-in-part of U.S. patent application Ser. No. 09/689,568, filed Oct. 12, 2000 and now U.S. Pat. No. 6,536,477, and further claims benefit of U.S. Provisional Patent Application Ser. No. 60/296,882, filed Jun. 7, 2001 and currently abandoned.

FIELD OF THE INVENTION

The present invention relates to microfluidic devices, and, more particularly, to modular microfluidic systems.

BACKGROUND OF THE INVENTION

There has been a growing interest in the manufacture and use of microfluidic systems for chemical and biochemical manufacturing processes and the acquisition of chemical and biological information. In particular, microfluidic systems allow complicated biochemical reactions to be carried out using very small volumes of liquid. These miniaturized systems increase the response time of the reactions, minimize sample volume, and lower reagent cost.

Traditionally, microfluidic devices and components have been constructed in a planar fashion using photolithography to define channels on a silicon or glass substrate followed by etching techniques to remove material from the substrate to form channels. More recently, a number of methods have been developed that allow microfluidic devices to be constructed from plastic, silicone or other polymeric materials. In addition to the use of traditional injection cavity molding, the wide variety of molding steps or methods (generally involving the construction of a negative mold and then inserting material into or over the mold) that have been developed for constructing microfluidic devices include: fabricating molds with silicon wafers (e.g., Duffy, et al., Analytical Chemistry (1998) 70:4974–4984 and McCormick, et al., Analytical Chemistry (1997) 69:2626–2630); building components using a LIGA technique (e.g., Schomburg, et al., Journal of Micromechanical Microengineering (1994) 4:186–191) as commercialized by MicroParts (Dortmund, Germany); and combining LIGA fabrication steps with hot-embossing techniques, as performed by Jenoptik (Jena, Germany). Imprinting methods for producing microfluidic devices in PMMA have also been demonstrated (e.g., Martynova, et al., Analytical Chemistry (1997) 69:4783–4789). Still further methods for constructing other types of microfluidic devices have been provided, by the same applicant herein, in two published WIPO PCT patent applications, Nos. PCT/US00/27313 (WO 01/25137) and PCT/US00/27366 (WO 01/25138). Such methods include construction of microfluidic devices using circuit board and sandwiched stencil fabrication methods.

U.S. Pat. No. 6,086,740 to Kennedy, entitled "Multiplexed Microfluidic Devices and Systems," (the "Kennedy Patent") discloses a 'multiplexed' microfluidic system for performing multiple fluidic operations in parallel. Multiple microfluidic modules are permanently connected a substrate, with each module sharing a common or connected input element. A single sample can be injected into all of the modules from a common port to perform multiple parallel analyses. Devices constructed according to the Kennedy patent, however, suffer from limited utility. For example, such devices lack fluidic connections between modules to perform sequential operations on a particular fluid with different modules. Further, no provisions are made in such devices to permit modules to be reconfigured, as may be desirable for experimental use or for optimizing fluid manipulation processes. Additionally, microstructures in devices constructed according to the Kennedy patent are constructed with surface micromachining techniques, which are time-consuming, capital-intensive, and not well-suited for generating devices in both low and high volumes.

Thus, there exist several different types of microfluidic devices that may be manufactured according to several different techniques. Despite the desirability of interconnecting or integrating such devices, however, to date no simple interconnection or integration methods or devices have been available. For example, a preparation system may be constructed using silicon fabrication technology while a sorting device might be constructed using a silicone replication technique (see, Fu, et al., Nature Biotechnology (199) 17:1109–1111). Though it would be desirable to combine such preparation and fabrication devices in a single integrated device, it would be difficult, if not impossible, to accomplish.

Moreover, discrete microfluidic components that perform specialized functions are often constructed. It would be desirable to quickly integrate such components into a complete system. For example, a silicon-based microfluidic sample preparation component can be constructed. A microfluidic detection component could also be separately constructed. To make a completed device, the developer must typically go back to the development stage and develop processing techniques and steps that allow a single integrated device to be developed.

Another issue in the development of microfluidic systems is the manner in which fluids and samples are introduced into and removed from a microfluidic device or system. It would be desirable to provide interface means that would permit fluids to be quickly and simply introduced or removed from such devices, and particularly for such an interface to be compatible with various types of microfluidic devices.

A need exists for a device or method for connecting together different types of microfluidic devices, such as may have been manufactured using different techniques. A further need exists for integrating discrete microfluidic components into a complete system. A still further need exists for aiding in the introduction and removal of fluids to and from microfluidic devices or systems.

A need also exists to provide a microfluidic system capable of fluidically connecting various modules to perform a sequence of operations on a fluid. Further utility could be gained if such a system were reconfigurable.

SUMMARY OF THE INVENTION

In a first separate aspect of the invention, a modular microfluidic system for performing a sequence of operations includes multiple microfluidic modules. Each module is capable of performing at least one operation in the sequence of operations, and the modules are fluidically coupled to perform the operation.

In another separate aspect of the invention, a modular microfluidic system for performing a sequence of operations on a fluid includes multiple microfluidic modules each fabricated with at least one stencil layer having a microfluidic structure defined through the entire thickness of the stencil layer. Each module is capable of performing at least one operation of the sequence of operations. The system further includes a microfluidic coupling device fabricated with at least one stencil layer having a microfluidic structure defined through the entire thickness of the stencil layer. The modules are fluidically coupled to perform the sequence of operations.

In another separate aspect of the invention, a method for performing a selected sequence of operations on a fluid includes the steps of identifying the operations of a sequence of operations, providing multiple microfluidic modules each capable of performing at least one operation of the sequence, fluidically coupling the modules to enable the sequence of operations to be performed, and providing at least one fluid to a module.

In another separate aspect of the invention, any of the foregoing aspects may be combined for additional advantage.

These and other aspects and advantages of the invention will become apparent to the skilled artisan upon review of the appended description, drawings, and claims.

BRIEF DESCRIPTION OF THE DRAWINGS

FIG. 1A is an exploded perspective view of a three-layer microfluidic coupling device.

FIG. 1B is a top view of the assembled device of FIG. 1A.

FIG. 1C is an exploded perspective view of a four-layer microfluidic coupling device.

FIG. 1D is a top view of the assembled device of FIG. 1C.

FIG. 2B is a top view of the assembled system components of FIG. 2A.

FIG. 3A is an exploded perspective view of at least a portion of a modular microfluidic system including a three-layer microfluidic distribution device or module, a four-layer microfluidic filtering device or module, three microfluidic coupling devices for coupling the distribution and filtering devices, and six microfluidic coupling devices to be connected to outputs of the filtering device.

FIG. 3B is a top view of the assembled system components of FIG. 3A.

FIG. 4A is an exploded perspective view of at least a portion of a modular microfluidic system including a fluidic introduction device or module, an input microfluidic coupling device, a microfluidic distribution device or module, and three output microfluidic coupling devices.

FIG. 4B is a perspective view of the assembled system components of FIG. 4A.

FIG. 5A is an exploded top perspective view of a modular microfluidic system including three modules fluidically coupled to one another with a multi-layer interconnecting base, the base having integral electrodes disposed in its lowermost layer.

FIG. 5B is a bottom perspective view of the lowermost device layer or chip showing wire traces for the integral electrodes.

FIG. 5C is a top perspective view of the assembled system components of FIG. 5A.

FIGS. 6A–6F are schematic views illustrating six different configurations of a modular microfluidic system for performing a sequence of operations on a fluid with three microfluidic modules, with the modules being connected using multiple microfluidic coupling devices.

FIG. 7A is a schematic of a modular microfluidic system having multiple microfluidic modules fluidically coupled to one another with an interconnecting base to perform a sequence of operations on a fluid.

FIG. 7B is a schematic of a modular microfluidic system having multiple microfluidic modules fluidically coupled to one another with multiple fluidic couplers to perform a sequence of operations on a fluid.

FIG. 8 is a schematic of a modular microfluidic system for performing a sequence of operations including three parallel, distinct sub-sequences.

DETAILED DESCRIPTION OF PREFERRED EMBODIMENTS OF THE INVENTION

Definitions

Figure 2A:
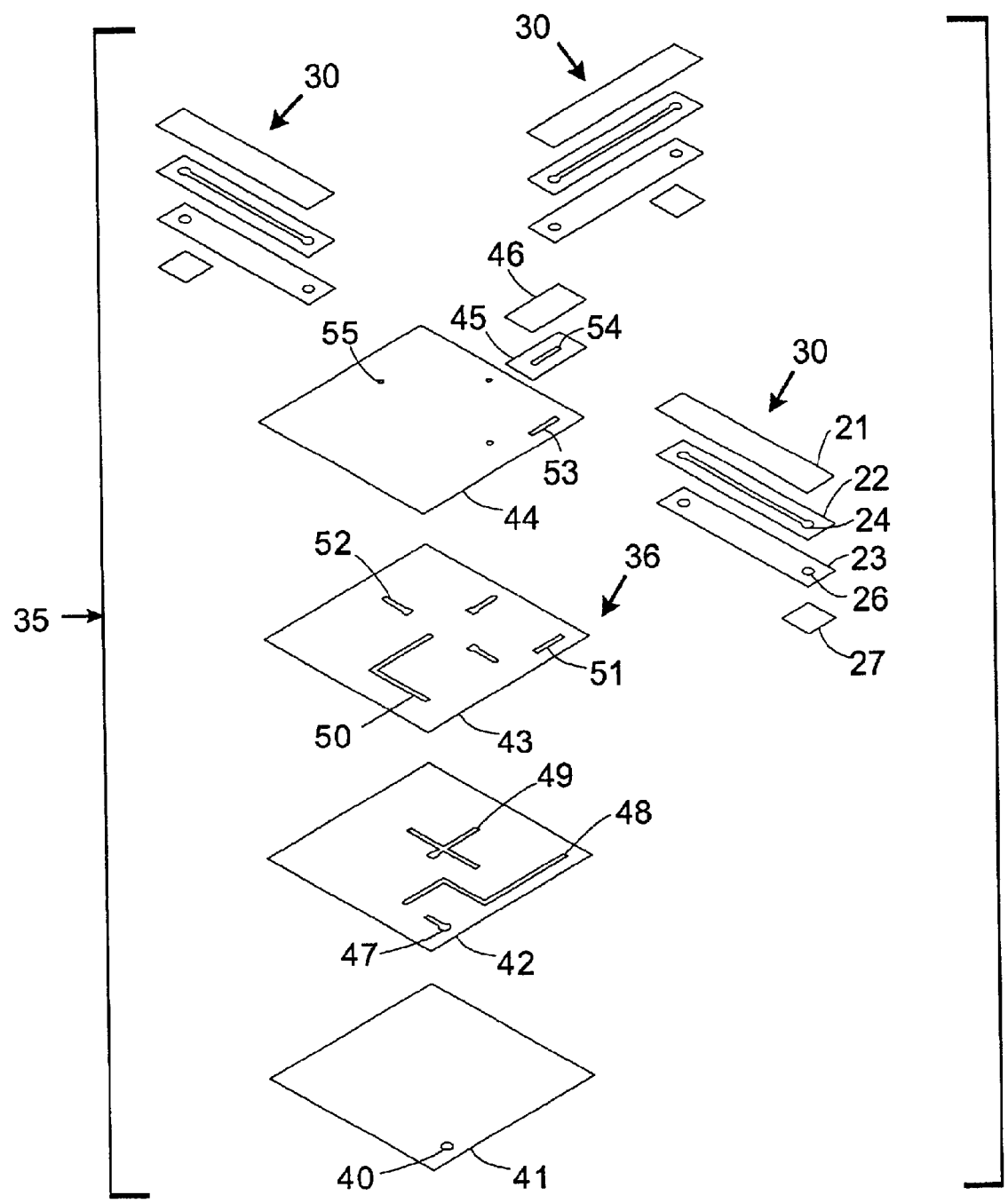
FIG. 2A is an exploded perspective view of a portion of a modular microfluidic system including a four-layer microfluidic metering device or module and three microfluidic coupling devices.

The term "channel" or "chamber" as used herein is to be interpreted in a broad sense. Thus, it is not intended to be restricted to elongated configurations where the transverse or longitudinal dimension greatly exceeds the diameter or cross-sectional dimension. Rather, such terms are meant to include cavities or tunnels of any desired shape or configuration through which liquids may be directed. Such a fluid cavity may, for example, comprise a flow-through cell where fluid is to be continually passed or, alternatively, a chamber for holding a specified, discrete amount of fluid for a specified amount of time. "Channels" and "chambers" may be filled or may contain internal structures comprising valves or similar fluidic components.

The term "fluidically coupled" as used herein means linked to permit fluid to pass from one element to another.

The term "microfluidic" as used herein is to be understood, without any restriction thereto, to refer to structures or devices through which fluid(s) are capable of being passed or directed, wherein one or more of the dimensions is less than 500 microns.

The term "module" as used herein refers to a discrete microfluidic component or microfluidic device that may be utilized within a microfluidic system. Preferably, microfluidic modules may be interconnected in various ways using microfluidic coupling devices.

The phrase "substantially planar" as used herein refers to a structure having a height of between about 1 and 500 microns and a length and width each at least 100 times larger than the height.

A "stencil layer" as used herein refers to a discrete layer of material through which a channel or aperture has been cut through the entire thickness of the layer. The outlines of the cut or otherwise removed portions form the lateral boundaries of microstructures, preferably microfluidic channels, that are formed by sandwiching one or more stencil layers between other stencils and/or substrates. The stencils and substrates are preferably substantially planar. Stencil layers are bonded by any technique that results in substantially liquid-tight channels within the device.

Microfluidic Devices

According to the present invention, modular microfluidic systems may include one or more microfluidic coupling devices that are used to communicate fluid between multiple microfluidic modules. The coupling devices may be used for the introduction of fluid into and removal of fluid from microfluidic modules, or for the integration of modular microfluidic systems.

Microfluidic modules or devices according to the present invention may be fabricated in various ways using a wide variety of materials. In a preferred embodiment, microfluidic modules according to the present invention are constructed using stencil layers to define structures such as channels and/or chambers by removing material through the entire thickness of the layer. A stencil layer is preferably substantially planar and has a channel or chamber cut through the entire thickness of the layer. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely-dimensioned microstructures, the use of a laser to cut a stencil layer inherently involves the removal of some material. Further examples of methods that may be employed to form stencil layers include conventional stamping or die-cutting technologies. The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices using sandwiched stencil layers, including polymeric, metallic, and/or composite materials, to name a few.

Various means may be used to seal or bond layers of a device together. For example, adhesives may be used. In one embodiment, one or more layers of a device may be fabricated from single- or double-sided adhesive tape, although other methods of adhering stencil layers may be used. A portion of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thicknesses of these carrier materials and adhesives may be varied.

In another embodiment, device layers may be directly bonded without using adhesives to provide high bond strength (which is especially desirable for high-pressure applications) and eliminate potential compatibility problems between such adhesives and solvents and/or samples. Specific examples of methods for directly bonding layers of nonbiaxially-oriented polypropylene to form stencil-based microfluidic structures are disclosed in copending U.S. provisional patent application No. 60/338,286 (filed Dec. 6, 2001), which is hereby incorporated by reference. In one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately 5 hours at a temperature of 154° C. to yield a permanently bonded microstructure well-suited for use with high-pressure column packing methods.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Referring to FIGS. 1A–1B, a microfluidic coupling device 20 having a substantially planar first substrate layer 21 and a substantially planar second substrate layer 23 is provided. The second substrate layer 23 has a lower surface that defines the bottom of the microfluidic coupling device 20. The coupling device 20 also has at least one substantially planar stencil layer 22 disposed between, or "sandwiched" between, the first and second substrate layers 21, 23. The stencil layer 22 has at least one channel 24 formed in it, with at least one dimension less than about 500 microns. The channel 24 is in fluid communication with a first aperture or fluid port 25 defined in the second substrate layer 23. The channel 24 is preferably vented to allow fluid to flow. Although not required in all embodiments, the coupling device 20 contains a second aperture or fluid port 26 in the second substrate layer 23. The second fluid port 26 is in fluid communication with the channel 24. In some embodiments, the second fluid port 26 may be defined in the first substrate layer 21. Alternatively, all or a portion of either substrate layer 21, 23 can be a semi-permeable membrane that allows the passage of gas, but substantially prevents the passage of liquids.

For devices of the type shown in FIGS. 1A–1B, adjacent surfaces of the various layers are complementary so as to seal against a sandwiched stencil layer. Notably, one or more stencil layers may be provided in a single coupling device. For example, combinations of mating layers may include substrate-stencil-substrate, substrate-stencil-stencil-substrate, or many others. Stencil and substrate layers may be stacked or layered to provide a complex microfluidic device. Most preferably, the mating layers are substantially planar. Stencils and substrate layers may be constructed from any suitable materials, including preferably MYLAR®, polyester, polyimide (e.g., KAPTON®) and adhesive tapes. One or more materials are preferably used to coat, seal, and/or adhere the channels formed between the substrates. Where the layers are constructed from adhesive tapes, the tapes can be pressure-curing tapes, temperature-curing tapes, chemical-curing tapes, light-curing tapes, or other types of curing tapes.

In one embodiment, one or more stencil layers are fabricated from single- or double-sided adhesive tape. A portion of the tape (of the desired shape and dimensions) can be cut through the thickness of the tape and removed to form, for example, a channel or entry/exit ports. The tape stencil can then be arranged between one or more supporting substrates or other stencil layers. In one embodiment, similarly-configured stencil layers can be stacked on one another. In this embodiment, the thickness or height of the resulting channels can be varied by simply varying the thickness of the stencil. If a tape stencil is used, then the total thickness includes the thicknesses of both the tape carrier and the adhesive or glue thereon.

In certain embodiments, double-sided tape may be used in constructing the coupling devices, and various substrate materials may be used for the other stencil layers. For example, in one embodiment configured as the coupling device 20 in FIGS. 1A–1B, stencil layer 21 is constructed from a MYLAR® material, stencil layer 22 from double sided tape and stencil layer 23 from single sided tape with a MYLAR® backing. In this manner, the upper and lower boundaries of the channel 24 are both MYLAR® material.

In a preferred embodiment, adhesive is used to connect a microfluidic coupling device to a separate microfluidic module or device. In a more preferred embodiment, the adhesive surface used to couple the microfluidic coupler to the microfluidic device is a non-permanent adhesive, such as are many types of pressure-sensitive adhesives. In this manner, a coupling device can be physically and fluidically connected to a microfluidic device, fluid may be communicated through the coupling device, and thereafter the microfluidic coupler may be removed. In another preferred embodiment, the surface used to couple the microfluidic coupling device to an external microfluidic device or module is made tacky with a substance such as silicone.

In one embodiment, the microfluidic coupling device is flexible. The entire coupling device can be constructed of various films, papers, tapes, plastics and the like such that the resulting coupling device is flexible. Flexibility can aid in aligning a microfluidic coupling device to another microfluidic device or can facilitate coupling two distinct microfluidic devices or modules. Materials used for fabricating a microfluidic coupling device may also be malleable. Such malleability aids in sealing a microfluidic coupling device with another device, especially in cases where the mating surface of the target device is uneven.

The microfluidic coupling device 20 of FIG. 1A can be constructed such that the lower surface of the second substrate 23 has an adhesive coating and such that one or more of the ports 25, 26 connects through the second substrate 23. Preferably, this adhesive coating is integral to the layer, such as provided by a self-adhesive tape. The device 20 also can be constructed such that the upper surface of the first substrate layer 21 has an adhesive, preferably self-adhesive, coating. In an alternative embodiment, a coupling device may be provided with two ports, the first port defined in the first substrate layer and the second port in the second substrate layer, with both the upper surface and lower surface having adhesive coatings. Such an embodiment allows the coupling device to be rapidly connected to external microfluidic devices or modules. The adhesive used may be either a permanent adhesive or a removable adhesive. In such an alternative embodiment, the device may also include a backing layer removably adhered to the adhesive lower surface of the second substrate. The backing material protects the adhesive material from inadvertent contact or adhesion with undesired objects until such a time as the microfluidic coupling device is to be attached to another microfluidic device. The backing material may be any suitable plastic, paper or foil.

In a further embodiment, a semi-permeable membrane permitting the passage of gases but substantially blocking the passage of liquids may be added to a microfluidic coupling device. Referring to FIGS. 1C–1D, for example, a microfluidic coupling device 30 is configured identically to the device 20 illustrated in FIGS. 1A–1B except for the addition of a semi-permeable membrane 27 covering the second fluidic port 26. The semi-permeable membrane 27 allows gases to pass, but substantially disallows the passage of liquid. For example, a suitable semi-permeable membrane will allow air to pass through it, but will not allow water to pass. The desired effect may be achieved by selecting a semi-permeable membrane with a suitable pore size. In one embodiment, the semi-permeable membrane 27 is a polymeric material with a pore size of less than about 75 microns, and preferably less than about 10 microns. Examples of such filter materials include Porex Technologies (Fairburn, Ga.) X-7744 (7 micron pore size) and GORETEX®-type materials.

With multiple ports provided in a single microfluidic coupling device, a first fluidic port may be used to admit liquid and a second fluidic port may be used as a vent for air escape. Alternatively, the second fluidic port may be used as a liquid exit port rather than a vent. A fluidic inlet port may be directly coupled to another microfluidic device or module using an adhesive. The adhesive may be disposed on a surface of the coupling device, on a surface of the target microfluidic device or module, or both.

In another preferred embodiment, porous materials can be used at the outlet of a microfluidic coupling device to add impedance to a fluidic system. These materials can be chosen so that they have slight resistances to the passage of air or gas, but provide very large resistance to the passage of liquid. The pore size and material composition can be selected to produce the desired effects and impedances. For a functional microfluidic device or module having multiple fluidic exit ports, multiple microfluidic coupling device may be used, with one coupling device associated with each exit port. One or more different coupling devices each having an outlet port may have porous materials associated with these outlet ports. Different porous materials may be associated the outlet ports of different coupling devices. In this manner, the coupling device outlet materials can be used to produce preferential fluid flow within a multi-outlet microfluidic device to which multiple coupling devices are connected.

Referring to FIGS. 1A and 1C, in a preferred embodiment the bottom surface of 28 of a microfluidic coupling device 20 or 30 is provided with an adhesive material adjacent to the first fluidic port 25 to allows the port 25 to be connected to the a fluidic exit port of a separate microfluidic device or module (not shown). Alternatively, the surface 28 can be non-adhesive yet still mate with an adhesive surface on the separate microfluidic device or module to which coupling is desired. In an alternative embodiment, mating surfaces of both a coupling device and a target microfluidic device or module are provided with adhesives.

An adhesive can be placed on the outer surface 28 of a microfluidic coupling device 20 or 30 in various ways. In a preferred embodiment, the bottom surface 28 of layer 23 is inherently adhesive, such as when the layer 23 is composed of self-adhesive tape with a downward-facing adhesive surface. In other embodiments, a coating may be placed on the bottom surface 28 of layer 23 either before or after assembly of the microfluidic coupling device. This coating can be accomplished in a number of ways, including spin coating, spray coating, and vacuum deposition.

In certain embodiments, it may not be desirable to have a fluidic port of a microfluidic coupling device open to the environment. Also, in some embodiments, a microfluidic coupling device may have a flap of material for sealing either the first or second fluidic port In a preferred embodiment, a port is disposed in an adhesive lower surface of a coupling device, and the flap is an extension of the second substrate.

Channels within microfluidic coupling devices according to the present invention may also be derivatized with a chemical or biological moiety in order to perform a binding or separation function. Referring again to FIG. 1A, a microfluidic coupler 20 may be constructed starting with an upper layer 21 constructed from a thin sheet of glass that is approximately ¼" (6 mm) wide by 1½" (49 mm) long by 1/32" (0.75 mm) thick. The stencil layer 22 may be constructed from 3.4 mil (83 microns) thick double-sided tape with a 40 mil (100 microns) wide channel. Finally, layer 23 may be constructed from a single-sided piece of adhesive tape with 0.08" (2 mm) diameter inlet/outlet ports 25, 26. Prior to assembly, the glass layer 21 may derivatized using a typical silanization reaction. Genetic probes can then be bound to the surface of the glass.

In operation, a fluidic sample is manipulated within a microfluidic module (not shown) and passed into the microfluidic coupling device 20. The sample may contain labeled genetic stands of interest that can bind to the surface of the derivatized glass 21. After incubation, the channel 24 of the microfluidic coupling device 20 may be washed to remove non-specifically bound material. The glass surfaces of the channel 24 can then be analyzed to determine if the labeled genetic material of interest is present. For instance, the genetic samples may be fluorescently labeled and the fluorescence of the channel studied. Notably, other types of surface chemistry may also be utilized, such as anti-body binding to polystyrene or Teflon or other materials.

In another aspect of the invention, a modular microfluidic system made from a plurality of microfluidic modules is provided. Preferably, each microfluidic module is adapted for rapid attachment to or detachment from one or more other modules, and is self-contained for performing a desired function independently of each other module. In a preferred embodiment, the microfluidic modules are attached to each other using the microfluidic coupling devices shown in FIGS. 1A–1D. As would be obvious to a skilled artisan, microfluidic modules may have one or more fluid inlet ports and one or more fluid outlet ports. In a preferred embodiment, these modular microfluidic systems can be made from modules that perform chemical or biochemical synthesis or chemical or biochemical analysis. The modular microfluidic systems may also be designed for use in either continuous processing mode or in batch processing mode.

As discussed in the background section above, microfluidic modules for use with the modular microfluidic systems may be constructed using various techniques, including photolithography/etching, micromolding, various LIGA methods (whether or not coupled with hot embossing), imprinting in PMMA, and by using circuit board and/or sandwiched stencil fabrication methods. The microfluidic modules are also capable of being used with a variety of pumping and valving mechanisms, including pressure, peristaltic pumping, electrokinetic flow, electrophoresis, vacuum and the like. Miniature pumps and valves may be constructed to be integral within such modules, although separate or off-line pumping or valving mechanisms are contemplated. In addition, the microfluidic modules are capable of being used in conjunction with optical detection (e.g., fluorescence, phosphorescence, luminescence, absorbance and colorimetry), electrochemical detection, and any of various suitable detection methods. Suitable detection methods will depend on the geometry and composition of the device. The choice of such detection methods will be within the purview of the skilled artisan.

Within existing technology, a microfluidic device typically performs a function on a sample and once that function is completed, it becomes necessary to transport the fluid off the device for further analysis. In a preferred embodiment of the present invention, a microfluidic multi-chip module (MCM) is constructed to facilitate transport of samples between more than one microfluidic module.

In one embodiment, one or more microfluidic coupling devices may be used to capture fluid that has been manipulated in a microfluidic device to promote further analysis or manipulation in a multi-step laboratory experiment. For example, FIGS. 2A–2B illustrate a microfluidic metering and coupling system 35 including a metering device 36 and three associated microfluidic coupling devices 30. The microfluidic metering device 36 is capable of receiving a quantity of sample having a large volumetric standard deviation, metering off a discrete amount having a much smaller volumetric standard deviation, dividing the metered amount into three equal components, and finally transporting the sample off-board for further analysis using the microfluidic coupling devices 30.

Referring to FIG. 2A, a metering device 36 useful with a modular microfluidic system is composed of six layers 41–46. The first layer is a ⅛" (3.2 mm) thick polycarbonate base 41 defining a fluidic inlet port 40. Five stencil layers 42–46 have channels 47–54 cut into them, with three fluidic outlet ports 55 defined in the third layer 44. Stencil layers 42–44 may be constructed from single-sided adhesive tape such as, for example, a 3 mil (76 micron) thick polypropylene carrier with permanent water-based adhesive. Smaller stencil layer 45 may be constructed from double-sided tape, such as, for example, 0.5 mil (13 microns) thick polyester carrier with acrylic adhesive on both sides. Further, stencil layer 46 may be constructed from a porous material such as 30–60 micron (pore size PTFE (Norton A-125). The stencil layers 42–46 are adhered together and onto the base layer 41.

The three microfluidic coupling devices 30 are constructed using stencil layers. A first layer 21 covers a channel 24 defined in a second layer 22 a 21–23, at least one of which may be composed of single-sided tape such as a 3 mil (75 micron) thick polypropylene carrier with water-based adhesive. The coupling devices 30 are 0.25" (6 mm) by 1–⅜" (34 mm) in dimension. A channel 24 that is 0.04" (1 mm) wide and 1–⅛" (28 mm) long is cut into the second stencil layer 22, and inlet and outlet ports 26 (0.08" or 2 mm diameter) are cut into the third stencil layer 23. A porous membrane 27 such as Norton G115 (1–2 micron pore size PTFE), cut into a ¼" by ¼" (6 mm by 6 mm) section, is adhered to the bottom surface third layer 23. All four layers 21, 22, 23, 27 are adhered together to form the assembled microfluidic coupling device 30.

A portion of an assembled modular microfluidic system 35 is shown in FIG. 2B. As assembled, the system portion 35 includes four different types of overlap regions 60–64 (overlaps 62 and 63 are identical) at the interfaces between fluidic structures disposed in different layers. Notably, each overlap region 60–64 provides an opportunity to form an impedance for controlling the movement of fluid within the device 36. If the overlap is very small in flow area, the impedance will be large, while if the overlap has a large flow area then the impedance will be smaller. These overlap-type impedance regions are particular useful in controlling developing flow, that is, flow that is progressing within the device along a liquid-gas (such as water-air) interface. All of the channels 47–54 are 3 mils (75 microns) high, thus the overlap regions are 6 mils (150 mils) high. At overlap 60, both channels are 40 mils (1000 microns) wide and they overlap for 40 mils (1000 microns). At overlap 61, channel 48 is 40 mils (1000 microns) wide and tapers down to 20 mils (500 microns) in the overlap region; channel 50 is 40 mils (1000 microns) wide and channel 48 extends across channel 50 for 20 mils (500 microns). At identical overlaps 62 and 63, the entry channels 48, 49 are 40 mils (1000 microns) wide, the exit portions are 70 mils wide (1000 microns) and the overlap is 40 mils (1000 microns) in length. The inlet ports 25 of the microfluidic coupling devices 30 are placed on top of the outlet ports of the microfluidic device 55 and the adhesive tape on the bottom surface of the microfluidic coupling devices 30 is used to seal the junction 64.

In operation, a sample plug is injected onto the microfluidic metering device 36 at the inlet port 40 using a syringe pump at a constant flow rate. A fluidic impedance 60 is constructed immediately after the inlet port 40 to control the initial fluid flow. The fluid then passes into channel 50 and fills the channel 50 until it reaches impedance 62. At this point, the excess fluid within the sample breaks through the microfluidic impedance at the overlap 61 before the microfluidic impedance at the overlap 62. The excess fluid passes down channel 48. Once all of the excess fluid has passed through the waste channels (48, 51 and 54) it reaches the porous material 46. The excess fluid will not pass the porous material 46 and the microfluidic impedance 62 is overcome. The amount of sample now ready for further manipulation is defined by the volume of channel 50 between the two microfluidic impedances 61 and 62. If a different sample volume is desired, then the position of the microfluidic impedance region 61 can be moved along channel 50 to alter the volume.

Once the air in channel 48 has been compressed sufficiently to build up enough pressure, microfluidic impedance 62 is overcome. The sample now enters chamber 49 and fills the entire chamber up to the impedances 63. Once this chamber has been completely filled, the output microfluidic impedances 63 are overcome and the samples enter into the inlet ports 55 of the microfluidic coupling devices 30 and enter into the channels 24 of the coupling devices 30. Once all of the coupling devices 30 are filled, the coupling devices 30 may be removed to permit the samples within the coupling device 30 to be analyzed with an "off board" technique, such as scintillation counting (e.g., for biomolecules labeled with 32P) or fluorescence analysis.

In another embodiment, a microfluidic system may utilize multiple sets of microfluidic coupling devices to interconnect multiple microfluidic devices or modules. For example, referring to FIG. 3A, a microfluidic system 65 includes a first set of coupling devices 20a to deliver fluid from a microfluidic distribution device or module 67 to a microfluidic filtering device or module 68, a second set of coupling devices 30 to control fluid flow, and a third set of coupling devices 20b to transport the fluid off the filtering device 68 for further analysis. The distribution device 67 may be constructed from a ⅛" thick polycarbonate base 71 defining an inlet port 70 and two stencil layers 72, 73. The stencil layer 72, 73, which define a channel 74 and exit ports 75, are constructed from single-sided adhesive tape consisting of 3 mil (75 micron) polypropylene carrier with a permanent water-based adhesive. The channel 74 is 500 microns wide and the outlet ports 75 are 0.08" (2 mm) diameter. The stencil layers 72, 73 are adhered together and onto the base 71.

A filtering device or module 68 may be similarly constructed by adhering three stencil layers 77–79 onto a ⅛" (3.2 mm) thick polycarbonate base 76. The stencil layers 77–79 define channels 80, 81, through-holes 82, 83, inlet ports 85 and outlet ports 84. All of the through-holes and ports are 0.08" (2 mm) in diameter.

The microfluidic couplers 30 are identical to those shown in FIGS. 2A–2B. The microfluidic couplers 20a, 20b are identical to the microfluidic couplers 30 with the exception that no porous material was added.

The assembled modular system 65 is shown in FIG. 3B and contains five different types of overlap regions 90–94. At overlap region 90, fluid passes from the distribution device 67 into microfluidic couplers 20a. At overlap region 91, fluid passes from the microfluidic couplers 20a into the filtering device 68. Two channels 80 and 81 overlap within the microfluidic filtering device 68 at overlap region 92. At overlap region 93, fluid passes from the microfluidic filtering device into the control microfluidic coupling devices 20b. At overlap region 94, fluid passes from the microfluidic filtering device 68 into the capture microfluidic coupling devices 30.

In operation, a sample plug is injected at the inlet port 70 using a syringe pump at a constant flow rate of 5 microliters per minute. The fluidic sample then passes into channel 74 where it is distributed among the three outlet ports 75. The fluid enters the microfluidic couplers 20a and is transported to the inlet ports 85 of the second device 68. The fluid passes across filter regions 86, bypasses the overlap region 92 and is transported to the exit region 93 into the control microfluidic couplers 20b. In the embodiment shown, the filter region 86 does not contain any filter material, although numerous types of filter materials could be added to the filter regions 86 by conventional means. Once sufficient fluid has passed into the control microfluidic couplers 20b, sufficient pressure may be applied to the outlets 26 to increase the pressure within the device 68 and overcome the impedance 92. The fluid then passes into the elution channel 81 and passes into the capture microfluidic coupling device 30. Once sufficient fluid has entered the capture microfluidic couplers 30 the devices can be removed from the microfluidic filtering device 68 for further analysis. An output port 26 of one of the coupling devices 20b, 30 can be blocked by folding such a device back on itself to cover the outlet port 26.

Microfluidic coupling devices according to the present invention can be used to supply fluids to an external microfluidic device and receive fluids from an external microfluidic device. Referring to FIG. 4A, a portion of a modular microfluidic coupling and distribution system 95 includes a microfluidic distribution device 67a constructed in the same manner as the device 67 shown in FIGS. 3A–3B. Also provided are microfluidic coupling devices 20c and 20d, which are substantially similar to the couplers 20b of FIGS. 3A–3B. A pipette tip coupling block 100 having a tapered fluid receptor 101 is connected to the coupler 20c and is shaped to fit a standard pipette tip 102 snugly. The assembled system portion 95 is shown in FIG. 4B. In use, the microfluidic coupler 20c is oriented with the ports facing upward, and the inlet port is connected to the outlet port 104 of the pipette tip coupling block 100. The outlet port of the microfluidic coupler 20c is connected to the inlet port 70 of the microfluidic distribution device or module 67a. A pipette tip 102 filled with liquid is inserted into the pipette tip coupling block 100. Fluid is injected from the pipette through the coupling block 100, through the coupling device 20c, into the distribution device 67a, and finally through the outlets ports 73 into the output microfluidic coupling devices 20d. Thereafter, the microfluidic coupling device 20c may be removed from the pipette tip coupling block 100 and another separate microfluidic device (not shown) can be connected to the coupling block 100 in a similar manner.

In alternative embodiments, coupling blocks can be constructed to permit introduction using various methods or structures, e.g., capillary tubes. In certain embodiments, a negative pressure can be applied at one or more the outlet ports of a microfluidic device to draw the fluid through a microfluidic coupler and into the device. If desired, small aliquots of fluid can be inputted in this manner.

In a further embodiment, a modular microfluidic system includes an interconnecting base that may contain electrodes to perform various types of detection and or electroactive manipulation. Referring to FIG. 5A, an interconnecting base 146 is constructed from three layers 130, 131, 140 and is capable of joining three distinct microfluidic modules 120–122. The base 146, which includes an electrode-bearing lower device layer or chip 140, a stencil layer 131, and a cover layer 130 having fluid ports 132, serves as a microfluidic coupling device for the three microfluidic modules 120–122. The distinct microfluidic modules 120–122 could be constructed from any number of different manufacturing techniques including silicon fabrication techniques, silicone replications, hot embossing, molding, injection molding, etc. These modules 120–122 can perform a variety of fluidic functions. A first microfluidic module 120 has an inlet port 123 on the bottom side and an exit port 124 on the top side. A second microfluidic module 121 has both inlet port 125 and exit port 126 on the bottom side. A third microfluidic module 122 has an inlet port 127 on the top side and an exit port 128 on the bottom side.

Referring to FIGS. 5A–5B, the lower device layer 140 of the base 146 contains electrodes 141 that may be constructed using circuit board technology. In this instance, the lower device layer 140 is preferably a circuit board substrate. The top surface 142 of the lower layer 140 forms the lower boundary of microfluidic channels 133, 134 defined in the stencil layer 131 in the assembled system 115 (as shown in FIG. 5C). Electrodes 141 are placed along the endpoints and center of each channel 133, 134. The electrodes 141 are made by forming holes in the lower device layer 140 in positions where the electrodes 141 are to be located, followed by soaking the substrate 140 in a copper solution to cover the inside surfaces of the holes, then patterning and etching the bottom surface and top surface to form copper lines on the bottom side 144 and electrodes 141, 143 on both sides. Finally, a conductive epoxy may be then screened into the holes that are to form the electrodes 141. Gold is preferably plated onto the electrodes 141 to form a well-defined electrode surface and the edges of the electrodes 141 may be covered with a layer of solder mask, if so desired. In this manner, the upper surface of the top layer 142 can actually be solder mask rather than the circuit board substrate itself.

In addition to the circuit board lower layer 140, the base 146 includes a stencil layer 130 and a cover layer 131. The stencil layer 131, which defines two channels 133, 134, may be constructed from single sided tape such as 2 mil (50 micron) polyester carrier with an acrylic adhesive. The cover layer 130, which defines various inlet/outlet ports 132, may be constructed from double sided adhesive, such as 0.5 mil (13 micron) polyester carrier with acrylic adhesive on both sides. The microfluidic interconnecting base 146 is assembled by adhering the two stencil layers onto the lower circuit board layer 140. The microfluidic modules 120–122 can then be fluidically coupled by affixing them to the interconnecting base 146.

The assembled modular microfluidic system 115 is shown in FIG. 5C. In use, fluid is injected into the inlet port 127 of device 122. The third module 122 acts on the fluid to perform a first operation. The fluid then leaves the outlet port 128 and enters the channel 134 of the interconnecting base 146. The fluid passes through channel 134 and enters the second module 121 at inlet port 126. The second module 121 performs a second operation and the fluid exits at port 125. The fluid enters the second channel 133 of the interconnecting base 146 and passes into the inlet port 123 of the first module 120. The first module 120 performs a third operation on the fluid and thereafter the fluid exits at exit port 124. The electrodes 141 within the interconnecting base 146 may be used for a number of functions, such as inducing electrokinetic flow or electrophoresis, or providing electronic detection such as electrochemical detection or impedance measurements. The electrodes 141 of the base 146 can be connected to the outside world through an edge card connector, since the electrodes lead to plated pads 145 located on the back side of the circuit board substrate 140. These pads 145 are spaced with standard edge card spacing for convenient use.

The modular microfluidic system 115 is preferably to perform continuous processing. Alternatively, once the microfluidic modules 120–122 have performed their function, one or all of the modules can be removed from the system 115. The modules 120–122 can be reused in other configurations or discarded. The base 146 can be reused with new modules or discarded.

In an alternative embodiment, if no electrode manipulation or testing is required, then the lower layer 140 in FIGS. 5A–5C may simply be a solid layer. In a further alternative embodiment, a flex-tape circuit board can be provided for the lower layer 140 to render the entire base 146 flexible.

Two different configurations for fluidically coupling multiple microfluidic modules to perform a sequence of operations on a fluid are shown in FIGS. 7A–7B. FIG. 7A is a schematic of a modular microfluidic system 700 having multiple microfluidic modules 701–704 fluidically coupled to one another with an interconnecting base 705 to perform a sequence of operations on a fluid. In use, a fluid is supplied to the first module 701 through a fluid input 708 by way of the interconnecting base 705. The first module 701 performs first operation on the fluid, and the fluid is transported through the base to the second module 702, where a second operation is performed on the fluid. Similarly, the fluid is transported (by way of the base 705) to the third and fourth modules 703, 704, where third and fourth operations are performed, respectively. Following the sequence of operations, any resulting fluid(s) may be transported from the system 700 through a fluid output 709.

FIG. 7B is a schematic of a modular microfluidic system 720 having multiple microfluidic modules 721–724 fluidically coupled to one another with multiple fluidic couplers 725–727 to perform a sequence of operations on a fluid. The modules 721–724 may be physically mounted to an optional substrate or mounting base 730. In operation, a fluid is supplied to the first module 721 through a fluid input 728. The first module 721 performs first operation on the fluid, and the fluid is transported through a first coupler 725 to the second module 722, where a second operation is performed on the fluid. Similarly, the fluid is transported (by way of the couplers 726, 727) to the third and fourth modules 723, 724, where third and fourth operations are performed, respectively. Following the sequence of operations, any resulting fluid(s) may be transported from the system 720 through a fluid output 729.

In one embodiment, one or more microfluidic tools are integrated into modules, which may in turn be combined with other modules to form operative devices. One or more module combinations may be integrated into microfluidic devices, or combinations may be linked externally. For example, referring to FIGS. 6A–6F, multiple microfluidic modules 632, 634, 636 may be linked externally in various sequences using couplers 637. Providing discrete modules for performing different chemical or biochemical synthesis steps, wherein the modules interconnected in various arrangements by a user, permits reaction steps to be performed in a user-selected order. One benefit of this capability is that it enables each step in a multi-step synthesis reaction to be separately optimized. Preferably, modules are adapted to be removably coupled (e.g., by using non-permanent adhesive surfaces) to one another to enable a sequence of operations to be altered. For example, one or more modules may be added, removed, or exchanged.

While simple serial arrangements of only three modules are provided in FIGS. 6A–6F, more complex arrangements involving larger numbers of modules are contemplated, such as shown in FIG. 8. FIG. 8 provides a schematic of a modular microfluidic system 750 having nine fluidically coupled microfluidic modules 751–759 for performing a sequence of operations including three parallel, distinct sub-sequences. In use, a fluid may be introduced into the first module 751, which performs a first operation on the fluid. The first module 751 is fluidically coupled with a second module 752, which performs a second operation on the fluid. At least one portion of the second operation includes dividing the fluid into up to three portions, which may be supplied to the third, fifth, or seventh modules 753, 755, 757. Each of these three modules 753, 755, 757 is part of a distinct sub-sequence. Further operations are performed until the fluid portions reach the fourth, sixth, and ninth modules 754, 756, 759. As will be recognized by the skilled artisan, many different and more complex modular systems may be constructed.

In one embodiment, a method for performing a selected sequence of operations on a fluid includes the steps of identifying the operations of a sequence of operations, providing multiple microfluidic modules each capable of performing at least one operation of the sequence, fluidically coupling the modules to enable the sequence of operations to be performed, and providing at least one fluid to a module. Any of a large number of different fluidic operations is contemplated, including but not limited to: metering, reacting, directing and controlling flow, heating, cooling, mixing, splitting, diverting, filtering, condensing, incubating, separating, and catalyzing.

When aggressive solvents such as organic solvents will be used with a microfluidic module or device according to the present invention, it is desirable to construct the module or device using relatively inert materials. Preferable construction materials include, but are not limited to fluorinated polymers (including, for example, FEP and PTFE), polypropylene, and polyethylene. In preferred embodiments constructed from multiple material layers, including those produced with sandwiched stencil methods, however, inert materials are challenging to work with because they are difficult to bind together. Specifically, these materials are usually characterized by low surface energies. To raise the surface energies of such materials to promote bindability, they may be surface treated. Desirable methods of surface treatment include: corona/plasma discharge; chemical treatment; and physical treatment. In a preferred embodiment, a microfluidic device was constructed employing a direct bonding method by heating sandwiched 2-mil layers of corona-treated FEP using a hot press at approximately 430° F. and 60 psi for approximately 40 seconds. In a more preferred embodiment, plasma-treated fluorinated polymers may be used.

In embodiments utilizing adhesives to bond layers of a microfluidic device intended for use with aggressive solvents, relatively inert adhesives are preferably used. Such adhesives include epoxies, acrylics (including UV-curable acrylics), polyurethanes, hot-melt adhesives, and certain rubber-based adhesives. Additionally, the adhesive bond line exposed to solvent in the resulting device is preferably thin to minimize interaction between the solvent and the adhesive.

In a preferred embodiment, a stencil layer is a flexible or elastomeric material, such as silicone, viton, or rubber, so as to enable tools including valving and pumping mechanisms. Pressure or mechanical force can be applied to a flexible layer to cause local bending or deformation, thereby blocking or partially obstructing a channel or chamber located above or below the flexible layer.

In a preferred embodiment, material forming a stencil is applied onto the substrate in only certain desired areas using printing techniques, such as, for example, silk screening. The material is then "cured" to form the channels and/or chambers. Examples include the use of an activatable or curable polymer as the stencil material. Another example is the use of paint or ink as the material. One example is the use of a Thick Medium heat-set acrylic from Genesis Artist Colors (Indianapolis, Ind.). In another embodiment, the entire surface of one of the substrates is coated with the stencil material. The stencil is then cured in areas where it is to remain and the rest of the material can be removed. In this embodiment, a curable epoxy material may be used. In a more preferred embodiment, the epoxy is a UV-curable epoxy. Alternatively, a two-part epoxy can be used, where the first part is patterned into place and the entire device is then soaked in the second part that only adheres to the stencil material in certain areas.

The present invention described and claimed herein is not to be limited in scope by the specific embodiments herein disclosed, since these embodiments are intended merely to illustrate certain aspects of the invention. All equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The disclosures of all references cited herein are incorporated by reference in their entireties.

What is claimed is:

1. A method for performing a selected sequence of operations on a liquid sample, the method comprising the steps of:
   identifying the operations of a first sequence of operations;
   providing a plurality of microfluidic modules, each module being adapted to perform at least one operation of the first sequence of operations;
   fluidically coupling at least two modules of the plurality of microfluidic modules to create a first arrangement of modules that enables the first sequence of operations to be performed;
   providing at least one liquid sample to at least one module of the plurality of microfluidic modules;
   wherein the at least one operation of the first sequence of operations alters a characteristic of the at least one liquid sample and the characteristic of liquid sample that is altered is selected from the group consisting of: volume, temperature, composition and purity; and
   performing the first sequence of operations.

2. The method of claim 1 wherein the first sequence of operations is performed in a batch mode.

3. The method of claim 1 wherein the first sequence of operations is performed in a continuous processing mode.

4. The method of claim 1, further comprising the steps of:
   identifying a second sequence of operations;
   altering the first arrangement of modules and fluidically coupling at least two modules of the plurality of modules to form a second arrangement of modules that enable the second sequence of operations to be performed.

5. The method of claim 4 wherein the altering step includes any of: exchanging, adding, or subtracting at least one module of the plurality of modules.

6. The method of claim 1 wherein the step of performing the first sequence of operations includes heating, cooling or condensing the liquid sample.

7. The method of claim 1 wherein the step of performing the first sequence of operations includes metering or splitting the liquid sample.

8. The method of claim 1 wherein the step of performing the first sequence of operations includes reacting, mixing, incubating or catalyzing the liquid sample.

9. The method of claim 1 wherein the step of performing the first sequence of operations includes filtering or separating the liquid sample.

10. A modular microfluidic system for performing a sequence of operations on a liquid sample, the system comprising:
    a plurality of microfluidic modules, each module of the plurality of modules being adapted to perform at least one operation of the sequence of operations;
    wherein the plurality of modules are fluidically coupled to perform the sequence of operations;
    wherein the at least one operation alters a characteristic of the liquid sample; and
    wherein the characteristic of the liquid sample that is altered is selected from the group consisting of: volume, temperature, composition and purity.

11. The modular microfluidic system of claim 10 wherein each module of the plurality of modules is adapted to be removably coupled with at least one other module of the plurality of modules.

12. The modular microfluidic system of claim 11 wherein the sequence of operations may be altered by exchanging a module of the plurality of modules adapted to perform a first operation with a different module adapted to perform a second operation.

13. The modular microfluidic system of claim 11 wherein the sequence of operations may be altered by fluidically coupling an additional microfluidic module to at least one module of the plurality of microfluidic modules.

14. The modular microfluidic system of claim 11 wherein the sequence of operations may be altered by fluidically de-coupling a microfluidic module from the plurality of microfluidic modules.

15. The modular microfluidic system of claim 10, further comprising a plurality of microfluidic couplers.

16. The modular microfluidic system of claim 15 wherein each microfluidic coupler of the plurality of microfluidic couplers includes at least one sandwiched stencil layer defining a microfluidic channel.

17. The modular microfluidic system of claim 16 wherein each microfluidic coupler of the plurality of microfluidic couplers is substantially non-rigid.

18. The modular microfluidic system of claim 15 wherein each microfluidic coupler of the plurality of microfluidic couplers includes at least on surface having a non-permanent adhesive.

19. The modular microfluidic device of claim 15 wherein each microfluidic coupler of the plurality of microfluidic couplers is fabricated with self-adhesive tape.

20. The modular microfluidic system of claim 10, further comprising an interconnecting base defining a plurality of microfluidic channels, the base being adapted to provide fluid communication between at least two modules of the plurality of microfluidic modules.

21. The modular microfluidic system of claim 20 wherein the interconnecting base comprises multiple layers including at least one stencil layer, and each channel of the plurality of microfluidic channels is defined through the entire thickness of a stencil layer.

22. The modular microfluidic system of claim 20 wherein the interconnecting base includes at least one electrode.

23. The modular microfluidic system of claim 10 wherein the sequence of operations includes at least two parallel, distinct sub-sequences.

24. The modular microfluidic system of claim 10 wherein at least one module of the plurality of microfluidic modules is adapted to perform a chemical or biochemical synthesis process.

25. The modular microfluidic system of claim 10 wherein at least one module of the plurality of microfluidic modules is adapted to perform a chemical or biochemical analysis process.

26. A modular microfluidic system for performing a sequence of operations on a liquid sample, the system comprising:
    a plurality of modules, each module of the plurality of modules being adapted to perform at least one operation of the sequence of operations, each module including at least one first stencil layer having a characteristic thickness and defining a microfluidic structure through the entire thickness of the at least one first stencil layer; and
    a microfluidic coupling device including at least one second stencil layer having a characteristic thickness and defining a microfluidic structure through the entire thickness of the at least one second stencil layer;
    wherein the plurality of modules are fluidically coupled to perform the sequence of operations;
    wherein the at least one operation alters a characteristic of the liquid sample; and
    wherein the characteristic of the liquid sample that is altered is selected from the group consisting of: volume, temperature, composition and purity.

27. The modular microfluidic system of claim 26 wherein each module of the plurality of modules is adapted to be removably coupled with at least one other module of the plurality of modules.

28. The modular microfluidic system of claim 26 wherein the microfluidic coupling device comprises a substantially rigid interconnecting base defining a plurality of microfluidic channels, the base being adapted to provide fluid communication between at least two modules of the plurality of microfluidic modules.

29. The modular microfluidic system of claim 28 wherein the interconnecting base includes at least one electrode.

30. The modular microfluidic system of claim 26, further comprising a plurality of additional coupling devices, each additional coupling device including at least one third stencil layer having a characteristic thickness and defining a microfluidic structure through the entire thickness of the at least one third stencil layer.

31. The modular microfluidic system of claim 26 wherein the coupling device is substantially non-rigid.

32. The modular microfluidic system of claim 26 wherein the coupling device includes at least one surface having a non-permanent adhesive.

* * * * *